(12) United States Patent
Hedberg et al.

(10) Patent No.: US 7,483,742 B2
(45) Date of Patent: *Jan. 27, 2009

(54) DETECTION OF DIASTOLIC HEART FAILURE

(75) Inventors: Sven-Erik Hedberg, Kungsängen (SE); Anders Björling, Järfälla (SE); Maria Torpo, Sundbyberg (SE); Karin Ljungström, Hässelby (SE)

(73) Assignee: St. Jude Medical AB, Jarfalla (SE)

( * ) Notice: Subject to any disclaimer, the term of this patent is extended or adjusted under 35 U.S.C. 154(b) by 307 days.

This patent is subject to a terminal disclaimer.

(21) Appl. No.: 10/562,109

(22) PCT Filed: Apr. 26, 2004

(86) PCT No.: PCT/SE2004/000636

§ 371 (c)(1),
(2), (4) Date: Dec. 22, 2005

(87) PCT Pub. No.: WO2005/102451

PCT Pub. Date: Nov. 3, 2005

(65) Prior Publication Data

US 2006/0149327 A1   Jul. 6, 2006

(51) Int. Cl.
*A61N 1/00* (2006.01)
(52) U.S. Cl. .......................... 607/17; 607/23
(58) Field of Classification Search ............ 607/9, 607/17–24, 60
See application file for complete search history.

(56) References Cited

U.S. PATENT DOCUMENTS 5,476,483 A   12/1995 Bornzin et al.
6,438,408 B1   8/2002 Mulligan et al.
6,876,881 B2 *  4/2005 Baumann et al. .............. 607/18
7,363,077 B1 *  4/2008 Min et al. ....................... 607/9

FOREIGN PATENT DOCUMENTS

EP   0 591 642   4/1994

OTHER PUBLICATIONS

"Pathophysiological Characterization of Isolated Diastolic Heart Failure in Comparison to Systolic Heart Failure," Kitzman et al, Journal of the American Medical Association, vol. 288, No. 17 (Nov. 6, 2002), pp. 2144-2150.

* cited by examiner

*Primary Examiner*—George Manuel
(74) *Attorney, Agent, or Firm*—Schiff Hardin LLP

(57) ABSTRACT

An implantable medical apparatus for detecting diastolic heart failure, DHF, has a DHF determining device for determining at least one blood pressure parameter for detecting a DHF state of the heart of a patient. The DHF determining device includes a pressure measuring unit for measuring pulse pressure in a cardiac cycle for a predetermined workload situation of the patient as the blood pressure parameter, and a comparator compares the measured pulse pressure with a predetermined reference value. A pacemaker includes such an apparatus and a control unit that optimizes pacing therapy depending on the result of the comparison of the measured pulse pressures with the predetermined reference values. A corresponding method of detecting diastolic heart failure, DHF, includes the step of determining at least one blood pressure parameter for detecting a DHF state of the heart of a patient by determining, as said blood pressure parameter, the pulse pressure in a cardiac cycle for a predetermined workload situation of the patient, and the determined pulse pressure is compared with a predetermined reference value.

22 Claims, 4 Drawing Sheets

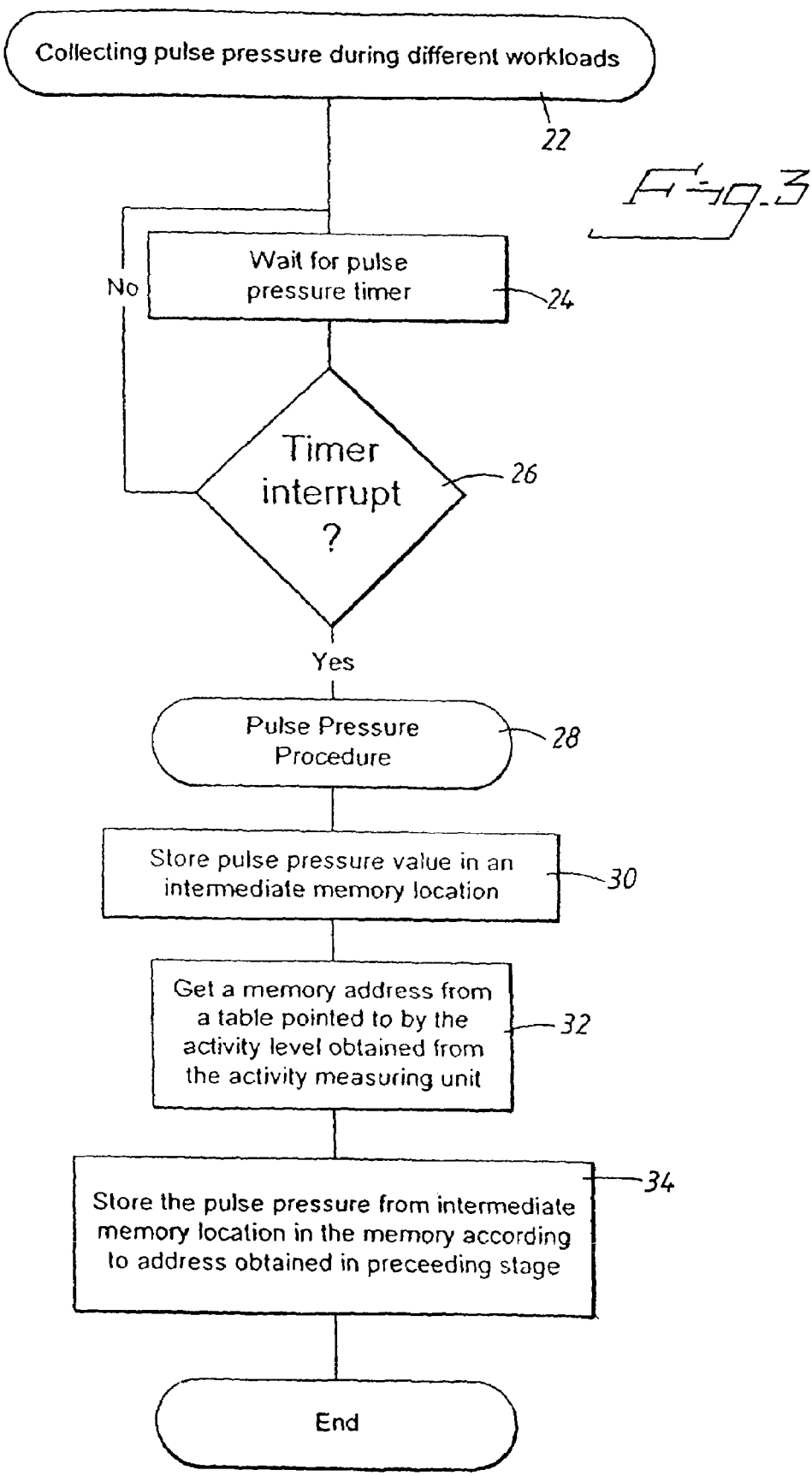

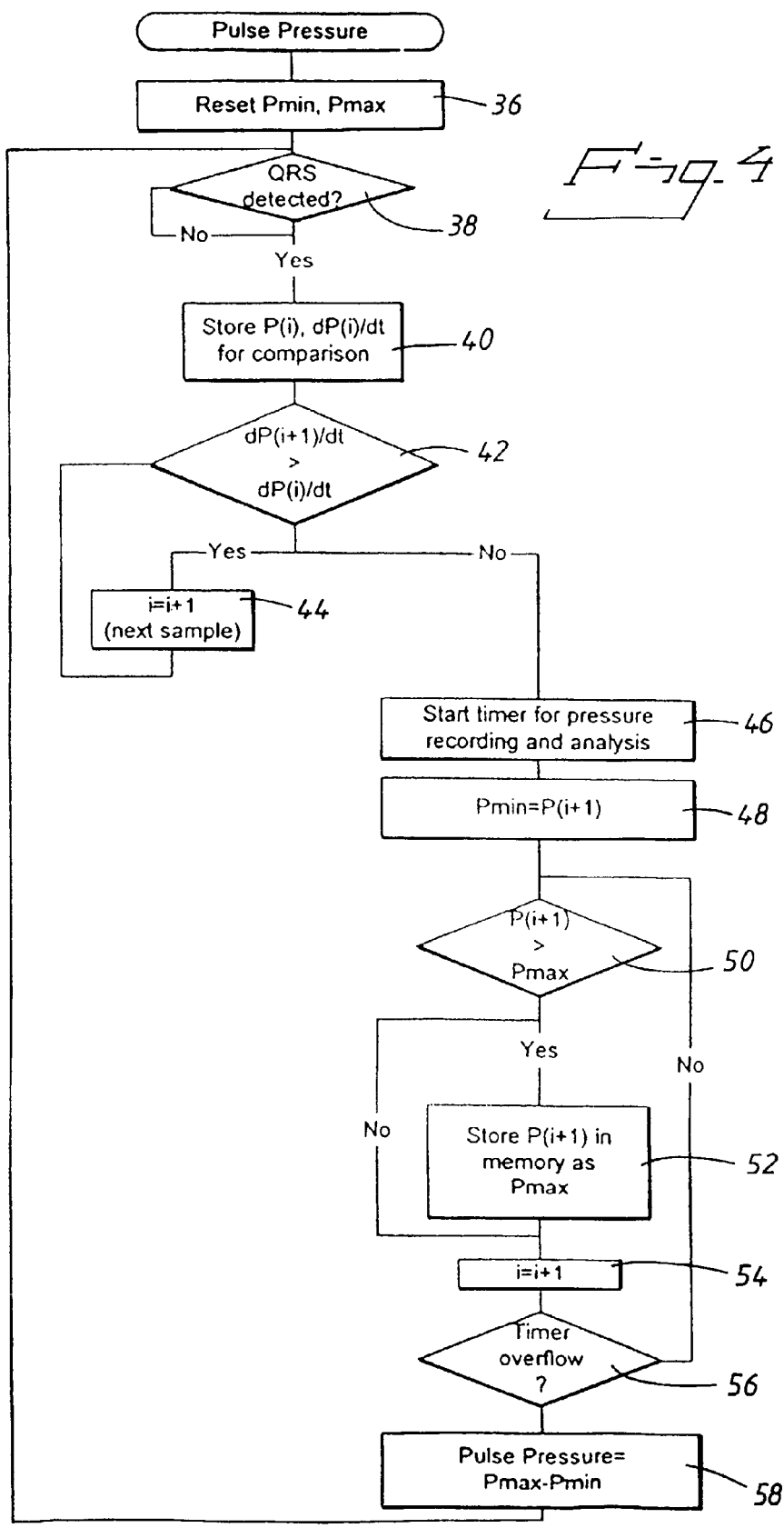

DETECTION OF DIASTOLIC HEART FAILURE

BACKGROUND OF THE INVENTION

1. Field of the Invention

The present invention relates to an implantable medical apparatus for detecting diastolic heart failure (DHF), of the type having a DHF determining device for determining at least one blood pressure parameter for detecting a DHF state of the heart of a patient. The invention also relates to a pacemaker provided with such an apparatus, and a method of detecting DHF, including the step of determining at least one blood pressure parameter for detecting a DHF state of the heart of a patient.

2. Description of the Prior Art

There is a growing recognition that congestive heart failure caused by a predominant abnormality in the diastolic function, i.e. diastolic heart failure, DHF, is both common and causes significant morbidity and mortality. Therefore early detection of DHF is important. Patients do not, however, seem to have symptoms at an early stage. In addition it has been hard to separate diastolic and systolic heart failure and they may also exist simultaneously.

It has been discovered that among the few parameters, separating diastolic heart failure from systolic heart failure, are certain blood pressure parameters obtained during work of the patient. Thus U.S. Pat. No. 6,438,408 describes an implantable medical device for monitoring congestive heart failure, CHF. A number of heart failure parameters indicative of the state of the heart failure are measured employing EGMs, blood pressures including absolute pressures, developed pressures (=systolic pressures−diastolic pressures) and the time derivative dP/dt, as well as heart chamber volumes. One of these parameters is the relaxation or contraction time constant $\tau$ of the heart chamber. This constant $\tau$ is calculated from a continuous pressure signal and is the drop in ventricular pressure at the end of systole and in the first part of diastole. The $\tau$ parameter is thus a general parameter reflecting the relaxation process.

SUMMARY OF THE INVENTION

Thus with the present invention the reduced peak and submaximal exercise performance of DHF patients is utilized for detecting DHF. With the technique according to the invention it is possible to detect DHF at an early stage, often before the patient seem to have any symptoms.

In the present invention the workload situation of the patient must be identified, and therefore, in an embodiment of the apparatus according to the invention, an activity sensor is provided for determining the workload of the patient.

In another embodiment of the apparatus according to the invention an averaging unit is provided to form an average value of pulse pressures during a plurality of cardiac cycles with the workload situation and an average value of pulse pressures measured during a number of cardiac cycles with the patient in rest. In this way the quality of the pulse pressure measurements is improved.

In other embodiments of the apparatus according to the invention a wireless communication unit is connected to the comparison unit for automatically sending the results of the comparison of measured pulse pressures with the reference values to an external receiver, or a memory is provided for storing the results of the comparison of measured pulse pressures with the reference values. Thus if the pulse pressure has risen above the reference value in a predetermined way this condition is automatically transmitted to a physician or stored for transmission in connection with a follow-up.

In other embodiments of the apparatus according to the invention, the pressure measuring unit includes a pressure sensor adapted for placement in right ventricle or coronary veins of the patient's heart, and the pressure measuring unit determines the maximum and minimum pressures in a cardiac cycle. It is preferred to place the pressure sensor in the right ventricle or the coronary veins, since the pressures in these places reflect the morphology of the left ventricular or aortic pulse pressure, especially with regard to maximum and minimum pressures.

The invention also relates to a pacemaker provided with the apparatus for detecting DHF and a control that optimizes pacing therapy depending on the result of the comparison of the measured pulse pressures with the predetermined reference values. The pressure measuring unit of the apparatus according to the invention then preferably includes a pressure sensor connected to the pacemaker, since it can monitor the pulse pressure of its carrier for long periods. This is an advantage since evolvement of DHF is a slow process.

In embodiment of the pacemaker according to the invention, a rate responsive sensor issued as an activity sensor for determining the workload situation of the patient. Even the pressure sensor of the pacemaker can be used as activity sensor.

In an embodiment of the method according to the invention, photo-plethysmographic signals are sensed for determining the pulse pressure, since it has been discovered that photo-plethysmographic signals obtained by a sensor placed close to the tissue where a pacemaker or ICD is implanted contain information about pulse pressure.

As mentioned above the measured pulse pressure is compared with a predetermined reference value, and in an embodiment of the apparatus and the method according to the invention the pulse pressure in a cardiac cycle is measured for a predetermined workload situation and a rest situation of the patient, and the difference between the pulse pressures measured in the workload and rest situations is compared with a predetermined reference value for the difference for DHF detection. A condition of DHF is identified by a higher pulse pressure during workload than a patient with a systolic heart failure would have. The reference value for detection of DHF is preferably obtained from measurements on the patient at an early stage of the implantation period of the apparatus or pacemaker. The patient is assumed not to suffer from DHF at the time of implantation. Therefore, in an embodiment of the method according to the invention, pulse pressures are measured for different workloads of the patient and for the patient in rest at an early time, when the patient is not suffering from DHF, for determining the reference values. These pulse pressures from an early stage can also be measured for a certain period of time and typical pulse pressures during an identified workload and during rest are gathered and averaged and then stored for later use as reference values for comparison purposes. If later the measured pulse pressure, or average pulse pressure measured during several cardiac cycles, exceeds the reference value determined in this way by a prescribed amount x %, this is used as an indication of DHF.

BRIEF DESCRIPTION OF THE DRAWINGS

FIG. 3 is a flow chart illustrating the overall collection of pulse pressure data in an embodiment of the apparatus according to the invention.

FIG. 4 is a flow chart showing details of an example of the procedure for obtaining pulse pressure data according to the present invention.

DESCRIPTION OF THE PREFERRED EMBODIMENTS

In the following an embodiment of the invention using a pressure sensor will be described, and the term pulse pressure means the varying pressure in aorta during a cardiac cycle.

Figure 1:
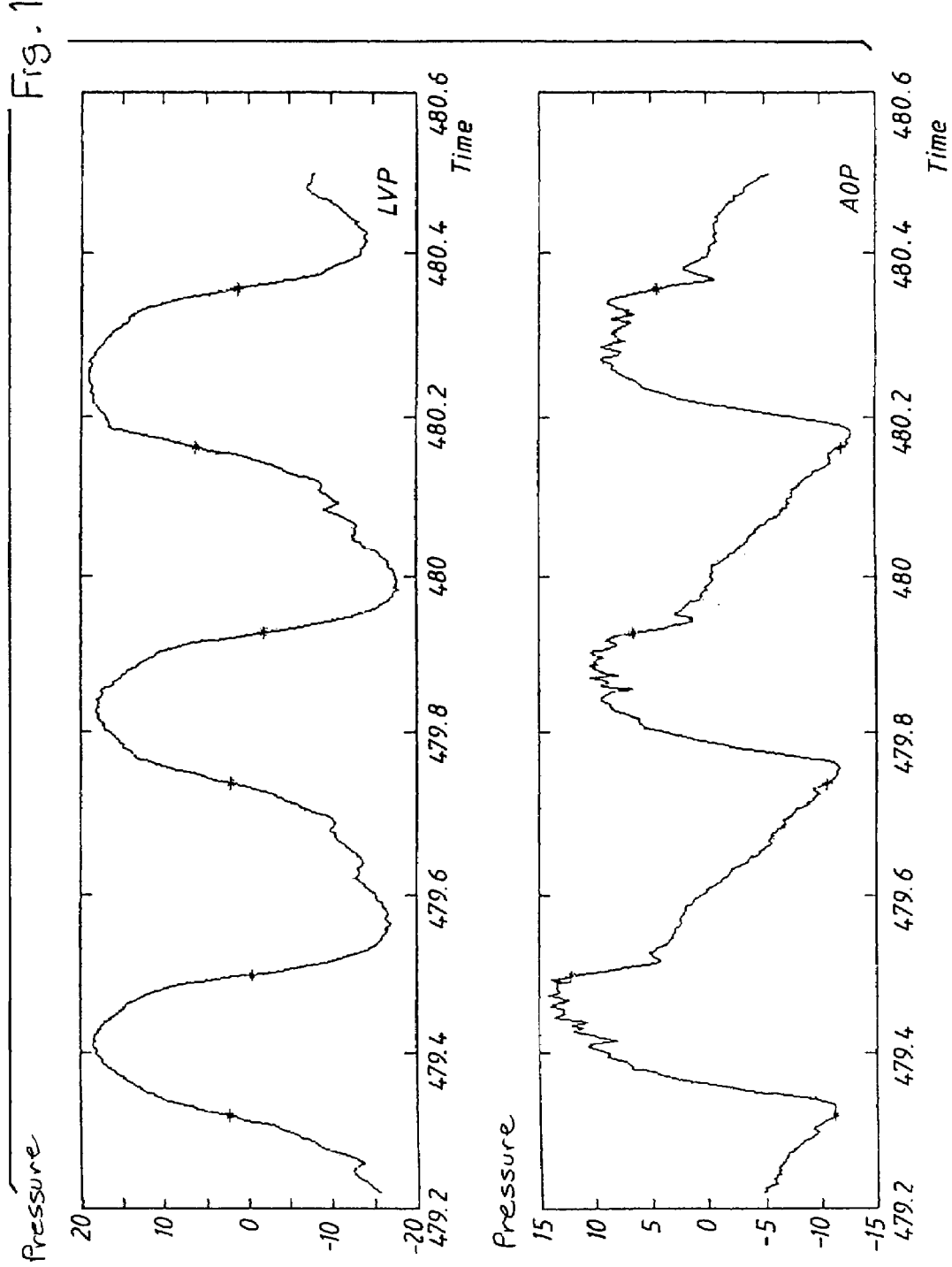
FIG. 1 is a diagram showing the left ventricular and aortic pressures as a function of time.

The above-mentioned pulse pressure can be obtained from the pressure measured in the left ventricle. In FIG. 1 the top curve shows the left ventricular pressure and the curve below the aortic pressure as a function of time. The magnitude of the pressures are indicated in arbitrary units in FIG. 1.

The asterisks in the curves of FIG. 1 denote time points for the maxima and minima of the time derivative of the left ventricular pressure, $dLVP/dt_{max}$ and $dLVP/dt_{min}$ respectively. As the aortic valves open close to the point $dLVP/dt_{max}$, the aortic pressure is close to the left ventricular pressure at this point of time.

During the period from $dlVP/dt_{max}$ to $dLVP/dt_{min}$ blood flows into aorta. The maximum of aortic pressure is situated in this period. The pulse pressure consequently can be obtained from the left ventricular pressure by subtracting the pressure at the point of $dLVP/dt_{max}$ from the maximum of the left ventricular pressure obtained during the mentioned period.

If the conditions are such that pressure signals from other parts of the hemodynamic system are morphologically similar to the left ventricular pressure, these signals can also be used for determining the pulse pressure in the present invention, since only relative changes have to be determined for detecting DHF.

Figure 2:
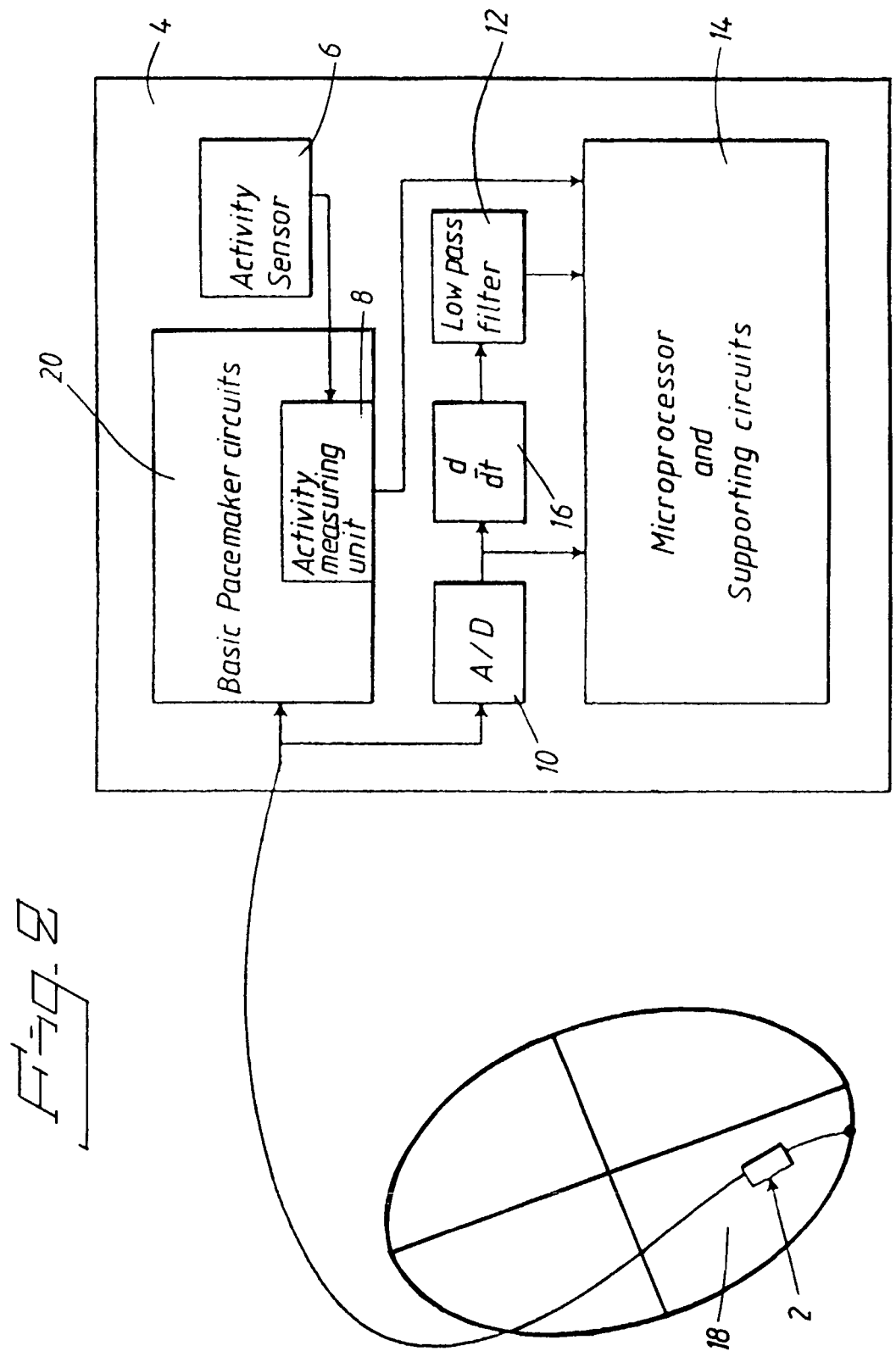
FIG. 2 is a block diagram of an embodiment of a pacemaker according to the invention.

FIG. 2 shows an embodiment of a pacemaker according to the invention comprising basic pacemaker circuits 20. A pressure sensor 2 is located in the right ventricle 18 of a patient's heart and connected to the pacemaker 4. The signals from the pressure sensor 2 are supplied to an A/D-converter 10. After A/D-conversion the time derivative of the signal is formed in a derivation unit 16. The time derivative of the pressure signals are filtered in the low pass filter 12 before supply to the microprocessor and supporting circuits 14. Since time derivation promotes high frequency noise, it is advisable to eliminate in this way possible false peaks and valleys, which could be interpreted as $dLVP/dt_{max}$ and $dLVP/dt_{min}$. The filtered signals are supplied regularly into a microprocessor and supporting circuits 14.

Located in the pacemaker 4 is an activity sensor 6 that is connected to an activity measuring unit 8 for determining the workload of the patient. A corresponding activity or workload signal is fed to the microprocessor and supporting circuits 14.

FIG. 3 is a flow chart illustrating an example of the overall process for collecting pulse pressure data. The development of DHF is a slow process as mentioned. A timer, at 26 in FIG. 3, is therefore provided for activating pulse pressure measurements on a regular basis for reducing the current drain and releasing microprocessor power.

Collection of pulse pressure data is performed for different workloads of the patient, at 22 in FIG. 3. As mentioned above the collection process is activated by a timer, at 26, and therefore the process has to wait for activation by the timer before starting, at 24. As the process is started, at 28, pulse pressure data are stored in different intermediate memory locations depending on the workload of the patient, at 30. Addresses to this memory locations are obtained from a table pointed to by the workload or activity measuring unit depending on the workload or activity, at 32. Pulse pressure data from the intermediate memory is then stored in another memory according to the address obtained in the preceding step for later analysis, at 34.

To improve the accuracy of the data stored the procedure of storing pulse pressure data can be performed by forming a floating mean value. One way to do this is to add a fraction 1/k of a new pulse pressure value P(i) to the pulse pressure value stored $P_{stored}$ at the memory location pointed to by the activity measuring unit and form a mean value $P_{store}$ according to the following equation $$P_{store} = \frac{P(i) + P_{stored} \times (k-1)}{k}$$

FIG. 4 is a flow chart illustrating in greater detail the procedure for obtaining the pulse pressure. $P_{max}$ and $P_{min}$ denote temporary storages of maximum and minimum aortic pressures.

In order to start the pulse pressure measurements a QRS has to be detected, at 38 in FIG. 4, after reset of $P_{max}$ and $P_{min}$, at 36. Pressure samples P(i) are then stored continuously together with the time derivative dP(i)/dt for comparison, at 40. A certain number of contiguous samples have to exist simultaneously, so that the above-mentioned filtering of the time derivative of the pressure is in accordance with the length of the filter coefficients. Care must be taken so that the delay in the filter influences the selection of corresponding pressure samples in a timely fashion, i.e. the pressure samples are selected with the same delay.

When $dP/dt_{max}$ has been found, at 42 and 44, the pressure at that point in time is selected as the minimum pressure $P_{min}$. The pressure then rises in the aorta and the maximum pressure during systole occurs in the period between $dP/dt_{max}$ and $dP/dt_{min}$, cf. the description of FIG. 1. In the process illustrated in FIG. 4 a simplified approach is used for determining maximum pressure $P_{max}$. Instead of determining the point of time for $dP/dt_{min}$ a timer is started at the point of $dP/dt_{max}$, at 46 in FIG. 4 and $P_{max}$ is determined according to steps 48, 50, 52, 54 till timer overflow, at 56. Such a timer procedure is justified since the systolic time period in practice varies little. The pulse pressure is then obtained by subtracting $P_{min}$ from $P_{max}$, at 58, which is the output of the process.

Instead of determining the pulse pressure with pressure sensors, it can be determined by photo-plethysmography. Photo-plethysmographic signals from a sensor placed close to the tissue at the location of the implanted pacemaker or ICD contains information on pulse pressure. Thus such photo-pletysmographic signals can be used as an alternative for determining the pulse pressure.

We claim:

1. An implantable medical apparatus for detecting diastolic heart failure (DHF), comprising:
    a workload detector configured to interact with a subject to detect a current workload of the subject;
    a pressure measuring unit configured to interact with the subject to measure pulse pressure, as a blood pressure parameter, in a cardiac cycle at said current workload of the subject, said pressure measuring unit emitting a pulse pressure signal indicative of said magnitude pulse pressure; and a comparator supplied with said pulse pressure signal that compares said magnitude of pulse pressure with a predetermined reference value that has a predetermined association with said current workload as a DHF predictor to produce a comparison result indicative of DHF state of the heart of the subject.

2. An apparatus as claimed in claim 1 wherein said pressure measuring unit also measures said magnitude of pulse pressure in a cardiac cycle for a rest situation of the subject as determined by said workload detector, and comprising a difference former that forms a difference between said magnitude of pulse pressure for said current workload and said magnitude of pulse pressure for said rest situation of the subject, and wherein said comparator compares said difference to said reference value to obtain said comparison result.

3. An apparatus as claimed in claim 1 wherein said workload detector comprises an activity sensor that detects an activity level of the subject and emits an activity signal representing said activity level, and a workload calculator supplied with said activity signal that determines said current workload of the subject from said activity signal.

4. An apparatus as claimed in claim 1 wherein said pressure measuring unit measures said magnitude of pulse pressure during a plurality of cardiac cycles, and comprising an averaging unit that forms an average value of the magnitude of pulse pressure measured during said plurality of cardiac cycles, and wherein said comparator compares said average value with said predetermined reference value to obtain said comparison result.

5. An apparatus as claimed in claim 1 comprising a wireless communication unit connected to said comparator that automatically wirelessly transmits said comparison result to an external receiver.

6. An apparatus as claimed in claim 1 comprising a memory connected to said comparator that stores said comparison result.

7. An apparatus as claimed in claim 1 wherein said pressure measuring unit comprises a pressure sensor configured for placement at a location selected from the group consisting of the right ventricle of the heart of the subject and coronary veins of the heart of the subject.

8. An apparatus as claimed in claim 1 wherein said pressure measuring unit measures a maximum of said magnitude of pulse pressure.

9. An apparatus as claimed in claim 1 wherein said pressure measuring unit measures a minimum of said magnitude of pulse pressure.

10. An apparatus as claimed in claim 1 wherein said pressure measuring unit comprises a sensor that emits photo-plethysmographic signals representing said magnitude of pulse pressure.

11. A pacemaker as claimed in claim 10 wherein said workload detector comprises an activity sensor that detects an activity level of the subject and emits an activity signal representing said activity level, and a workload calculator supplied with said activity signal that determines said current workload of the subject from said activity signal.

12. A pacemaker as claimed in claim 11 wherein said pressure measuring unit comprises a pressure sensor that measures said magnitude of pulse pressure, and wherein said pressure sensor also forms said activity sensor.

13. A method for detecting diastolic heart failure (DHF), comprising the steps of:
  determining a current workload of a subject;
  measuring a magnitude of a pulse pressure in vivo, as a blood pressure parameter, in a cardiac cycle of the subject for said current workload situation of the subject; and
  electronically comparing said magnitude of pulse pressure with a predetermined reference value that has a predetermined association with said current workload as a DHF predictor to produce an electronic comparison result indicative of a DHF state of the heart of the subject.

14. A method as claimed in claim 13 comprising also measuring said magnitude of pulse pressure in a cardiac cycle for a rest situation of the subject, and electronically forming a difference between said magnitude of pulse pressure for said current workload and said magnitude of pulse pressure for said rest situation of the subject, and wherein the step of comparing comprises comparing said difference to said reference value to obtain said comparison result.

15. A method as claimed in claim 13 comprising measuring said magnitude of pulse pressure during a plurality of cardiac cycles, and electronically forming an average value of the pulse pressure measured during said plurality of cardiac cycles, and wherein the step of comparing comprises comparing said average value with said predetermined reference value to obtain said comparison result.

16. A method as claimed in claim 13 comprising automatically wirelessly transmitting said comparison result to an external receiver.

17. A method as claimed in claim 13 comprising measuring said magnitude of pulse pressure using a pressure sensor placed at a location selected from the group consisting of the right ventricle of the heart of the subject and coronary veins of the heart of the subject.

18. A method as claimed in claim 13 wherein the step of measuring said magnitude of pulse pressure comprises measuring a maximum of said magnitude of pulse pressure.

19. A method as claimed in claim 13 wherein the steps of measuring said magnitude of pulse pressure comprises measuring a minimum of said magnitude of pulse pressure.

20. An apparatus as claimed in claim 13 wherein the step of measuring said magnitude of pulse pressure comprises measuring said magnitude of pulse pressure using a sensor that emits photo-plethysmographic signals representing said magnitude of pulse pressure.

21. A method as claimed in claim 13 comprising determining said magnitude of pulse pressure during said current workload situation of the subject at a time when the subject is not suffering from DHF, and determining said reference value from said magnitude of pulse pressure for said current workload when the subject is not suffering from DHF.

22. An implantable cardiac pacemaker comprising:
  a diastolic heart failure (DHF) determining device comprising a workload detector configured to interact with a subject to detect a current workload of the subject;
  a pressure measuring unit configured to interact with the subject to measure a magnitude of pulse pressure, as a blood pressure parameter, in a cardiac cycle for a said current workload of the subject, said pressure measuring unit emitting a pulse pressure signal indicative of said magnitude of pulse pressure, and a comparator supplied with said pulse pressure signal that compares said magnitude of pulse pressure with a predetermined reference value that has a predetermined association with said current workload as a DHF predictor to produce a comparison result indicative of a DHF state of the heart of the subject; and
  a therapy administration unit configured to interact with the heart of the subject to administer electrical cardiac therapy to the heart, said therapy administration unit being connected to said DHF determining device and being supplied with said comparison result therefrom, and administering said electrical cardiac therapy dependent on said comparison result.

* * * * *